United States Patent
Kwon et al.

(10) Patent No.: US 9,533,074 B2
(45) Date of Patent: Jan. 3, 2017

(54) GENE DELIVERY STENT USING TITANIUM OXIDE THIN FILM COATING, AND METHOD FOR FABRICATING SAME

(75) Inventors: Jin Sook Kwon, Gwangju (KR); Young Keun Ahn, Gwangju (KR); Myung Ho Jeong, Gwangju (KR); Sun Jung Song, Gwangju (KR); Dong Lyun Cho, Gwangju (KR)

(73) Assignee: Chonnam National University Hospital, Gwangju (KR)

( * ) Notice: Subject to any disclaimer, the term of this patent is extended or adjusted under 35 U.S.C. 154(b) by 240 days.

(21) Appl. No.: 13/993,896

(22) PCT Filed: Dec. 2, 2011

(86) PCT No.: PCT/KR2011/009298
§ 371 (c)(1),
(2), (4) Date: Oct. 8, 2013

(87) PCT Pub. No.: WO2012/081850
PCT Pub. Date: Jun. 21, 2012

(65) Prior Publication Data
US 2014/0018908 A1    Jan. 16, 2014

(30) Foreign Application Priority Data

Dec. 13, 2010 (KR) .......................... 10-2010-0127251
Nov. 22, 2011 (KR) .......................... 10-2011-0121949

(51) Int. Cl.
| A61L 27/00 | (2006.01) |
| A61L 27/54 | (2006.01) |
| A61L 31/02 | (2006.01) |
| A61L 31/16 | (2006.01) |

(52) U.S. Cl.
CPC .............. *A61L 27/54* (2013.01); *A61L 31/022* (2013.01); *A61L 31/16* (2013.01); *A61L 2300/22* (2013.01); *A61L 2300/236* (2013.01); *A61L 2300/252* (2013.01); *A61L 2300/258* (2013.01); *A61L 2300/416* (2013.01); *A61L 2300/802* (2013.01); *A61L 2400/18* (2013.01)

(58) Field of Classification Search
CPC ........... A61L 2300/22; A61L 2300/236; A61L 2300/252; A61L 2300/258; A61L 2300/416; A61L 2300/802; A61L 2400/18; A61L 27/54; A61L 31/022; A61L 31/16
USPC ......................................... 623/1.42; 427/2.25
See application file for complete search history.

(56) References Cited

U.S. PATENT DOCUMENTS

| 5,868,782 | A | 2/1999 | Frantzen |
| 6,599,314 | B2 | 7/2003 | Mathis |
| 7,005,137 | B1 | 2/2006 | Hossainy et al. |
| 2005/0119398 | A1* | 6/2005 | Zhang .................... B01J 19/088 524/497 |
| 2008/0033531 | A1 | 2/2008 | Barthel et al. |
| 2010/0228341 | A1* | 9/2010 | Weber ................... A61L 31/088 623/1.39 |

FOREIGN PATENT DOCUMENTS

| KR | 1992-0005257 A | 3/1992 |
| KR | 1999-0035927 A | 5/1999 |
| KR | 1999-0087472 A | 12/1999 |
| KR | 2000-0069536 A | 11/2000 |
| KR | 2002-0066707 A | 8/2002 |
| KR | 2002-0093610 A | 12/2002 |
| KR | 10-2004-0055785 A | 6/2004 |
| KR | 10-2007-0003172 A | 1/2007 |
| KR | 10-0752100 B1 | 8/2007 |
| KR | 10-2009-0037390 A | 4/2009 |

OTHER PUBLICATIONS

Klugherz, et al., Gene Delivery from a DNA Controlled-Release Stent in Porcine Coronary Arteries, 2000, 1181-1184, vol. 18.
Fishbein, et al., Bisphosphonate-Mediated Gene Vector Delivery from the Metal Surfaces of Stents, Proceedings of the National Academy of Sciences of the United States of America PNAS, Jan. 3, 2006, 159-164, vol. 103 No. 1.
Perlstein, et al., DNA Delivery from an Intravascular Stent with a Denatured Collagen-Polylactic-Polyglycolic Acid-Controlled Release Coating; Mechanisms of Enhanced Transfection, Gene Therapy, 2003, 1420-1428, vol. 10.
Kastrati, et al., Analysis of 14 Trials Comparing Sirolimus-Eluting Stents with Bare-Metal Stents, New England Journal of Medicine., Feb. 12, 2007, 1030-1039, vol. 356, No. 10.

* cited by examiner

*Primary Examiner* — Janet Epps-Smith
(74) *Attorney, Agent, or Firm* — The Webb Law Firm

(57) ABSTRACT

The present invention relates to a gene delivery stent using titanium oxide thin film coating and a method for fabricating the gene delivery stent. The gene delivery stent according to the present invention may be loaded with a drug having anti-inflammatory and anti-thrombotic effects and simultaneously deliver a gene capable of inhibiting proliferation of vascular smooth muscle cells. Accordingly, late thrombosis and metal allergy may be reduced, and vascular restenosis in the stent region may be prevented, thereby making it possible to increase treatment effects of the bare metal stent.

5 Claims, 12 Drawing Sheets

A: thermocouple
B: Pump
C: Bubbler
D: Ar
E: $O_2$
F: $N_2$
G: TitaniumWire
H: Stent Abciximab-beta gal ALA-beta gal Heparin-beta gal Drug B-beta gal Drug C-beta gal Drug D-beta gal

GENE DELIVERY STENT USING TITANIUM OXIDE THIN FILM COATING, AND METHOD FOR FABRICATING SAME

TECHNICAL FIELD

The present invention relates to a gene delivery stent using titanium oxide thin film coating and a method for fabricating the same.

BACKGROUND ART

A bare metal stent is an implantable material used for treatment purpose so as to increase a blood vessel diameter by being grafted at a disease site at which the blood vessel diameter is reduced caused by atherosclerotic plaque, neoplastic tissue, cruor, or the like, which blocks blood from flowing or allow the blood not to smoothly flow.

A disease in which this stent is mainly used is cardiovascular diseases, which account for 30% or more of causes of death in the world, and more than 17.5 million people have died every year due to these diseases. Ischemic cardiovascular diseases occupying the largest portion of the cardiovascular diseases as described above mean that problems (atherosclerotic plaque, neoplastic tissue, or cruor) are generated in a coronary artery supplying blood to heart muscle, and a method for treating ischemic heart disease is divided into a non-invasive method (drug therapy) and an invasive method (angioplasty). Among them, a bare metal stent used in conventional angioplasty, which is the invasive method, has an excellent treatment effect of enlarging a coronary artery diameter to fix the enlarged coronary artery diameter, but it was reported in academia and a clinical treatment field that restenosis occurring after the bare metal stent was grafted was the biggest problem.

A drug eluting stent (DES), which was developed in order to prevent restenosis as described above, significantly reduced a generation rate of restenosis in patents. However, in spite of incorporating the treatment using an anti-thrombotic agent (aspirin and clopidogrel), late thrombus formation that did not appear well in animal tests has appeared in patents after 3 or 5 years or more of the graft of the drug eluting stent. As the reason, a hypothesis that the drug eluting stent effectively inhibits proliferation or inflammation reactions of vascular smooth muscle cells but excessively inhibits growth of endothelial cells at the same time, and thus a re-endothelization process of covering a surface of the stent is delayed, which causes the late thrombus formation has been persuasively accepted until now.

For this reason, an effort to find an ideal method capable of not inhibiting growth of endothelial cells while inhibiting proliferation of vascular smooth muscle cells has been continuously made domestically and globally, but it is impossible to allow a drug used for the drug eluting stent to affect only a specific cell due to characteristics of a chemical material. Therefore, as an alternative, a treatment method using genes that may be relatively cell-specifically expressed has been suggested. In relation to this, various studies have been conducted domestically and globally, and as a result, a method of preparing a DNA controlled release stent by coating a surface of the stent using polylactic-polyglycolic acid (PLGA) and collagen-polylactic-polyglycolic acid together with each other among non-degradable polymers to discharge a GFP gene, which is a report gene, to the outside of the stent has been reported in 2000 (Gene Delivery from a DNA Controlled-Release Stent in Porcine Coronary Arteries, Bruce D. et al., NATURE BIOTECHNOLOGY, 2000, Vol. 18, 1181-1184; Bisphosphonate-Mediated Gene Vector Delivery from the Metal Surfaces of Stents, Ilia Fishbein et al., PNAS., 2006, Vol. 103, 159-164).

In addition, an effect of delivering iNOS genes to reduce formation of neointima by a method of coating a surface of a metal stent with polyalanine bisphosphonate (PAA-BP), which is an aqueous polymer, and then binding adenovirus thereto again using a binding agent was reported by Ilia Fishbein et al., in 2006, such that a possibility of inhibiting restenosis using the gene delivery stent was reported (DNA Delivery from an Intravascular Stent with a Denaturated Collagen-Polylactic-Polyglycolic Acid-Controlled Release Coating: Mechanisms of Enhanced Transfection, I Perlstein et al., Gene Therapy, 2003, Vol. 10, 1420-1428).

However, in most of the current technologies, in order to form a coating layer to which a gene complex may be bound on a surface of a metal so that the gene complex is adhered to a metal stent made of stainless steel, a non-degradable organic polymer or degradable collagen has been used, or in order to increase gene transfection efficiency, a viral vector has been used.

In the case of a technology of fabricating a gene eluting stent using the existing polymer, problems such as allergy, inflammation reactions, or the like, may be generated by the organic polymer, and it may be significantly difficult to find a polymer having excellent biocompatibility. In addition, in the case in which the stent is fabricated using the viral vector, it is still not free from a possibility of generating cancer and inducing immune reactions.

Therefore, introduction of another coating material for coating the gene complex has been demanded. Particularly, this coating layer should have an appropriate functional group to which the gene complex may be sufficiently bound, a uniform surface, and excellent biocompatibility such as an anti-thrombotic property, an anti-inflammatory property, and the like. In addition, only when a coated polymer layer has an excellent adhesive property with a substrate and excellent mechanical strength, the polymer thin film may endure a strong blood flow during a medical operation and disinfection process or after the medical operation for a long period of time.

Therefore, in order to increase a success rate of introducing the DNA Controlled-Release Stent, selection of a thin film material that does not have these problems and development of a coating technology thereof and a gene complex adhering technology are essentially demanded.

DISCLOSURE

Technical Problem

Therefore, the present inventors confirmed an effect of reducing late thrombosis or metal allergy by coating a surface of an implantable metal stent with titanium oxide, modifying a surface of a titanium oxide thin film coated with titanium oxide to adhere drug and genes onto the surface and an effect of preventing vascular restenosis in the stent region by making it possible to transfect genes capable of inhibiting growth of cells into the cells, thereby completing the present invention.

An object of the present invention is to provide a gene delivery stent using titanium oxide thin film coating capable of reducing late thrombosis or metal allergy and preventing vascular restenosis in the stent region by making it possible to transfect the gene capable of inhibiting growth of cells into the cells, and a method for fabricating the same.

Technical Solution

In one general aspect, there is provided a method for fabricating a gene delivery stent using titanium oxide thin film coating capable of reducing late thrombosis or metal allergy and preventing vascular restenosis in a stent region by making it possible to transfect the gene capable of inhibiting growth of cells into the cells.

In another general aspect, there is provided a gene delivery stent using titanium oxide thin film coating fabricated by the method as described above.

The gene delivery stent according to the present invention may include: a titanium oxide thin film made of titanium dioxide ($TiO_2$), $TiO_{2-x}N_x$ ($0.001 \leq x \leq 1$), or a mixture thereof and coated on a surface of a metal stent; a drug layer containing a drug having a function group bound to a hydroxyl group of the titanium oxide thin film in which the hydroxyl group is introduced by modifying a surface of the titanium oxide thin film to thereby be adhered onto the titanium oxide thin film; and an oligonucleotide layer containing oligonucleotide bound to the drug to thereby be adhered onto the drug layer.

In more detail, the gene delivery stent may be fabricated by uniformly coating the surface of the metal stent with the titanium oxide thin film made of titanium dioxide ($TiO_2$), $TiO_{2-x}N_x$ ($0.001 \leq x \leq 1$), or the mixture thereof at a thickness of 50 to 100 nm by a plasma enhanced chemical vapor deposition (PECVD) method, modifying the surface of the titanium oxide thin film by a plasma process using water in order to adhere a sufficient amount of gene complexes to introduce a hydrophilic functional group into the coated surface of the titanium oxide thin film, separately adhere at least one drug selected from abciximab (ReoPro), heparin, and alpha-lipoic acid (ALA) thereto, and physically adhere the gene onto the surface of the drug.

The gene delivery stent according to the present invention may have a titanium oxide thin film/drug/gene complex structure by being fabricated through the method as described above, wherein the complex structure has advantages in that a drug having anti-inflammatory and anti-thrombotic effects may be loaded and genes capable of inhibiting growth of vascular smooth muscle cells may be simultaneously delivered.

Hereinafter, the present invention will be described in detail.

The present invention provides a method for fabricating a gene delivery stent using titanium oxide thin film coating, the method including:

1) a titanium oxide coating step of coating the surface of the metal stent with titanium oxide represented by the following Chemical Formula 1;
2) a surface modifying step of modifying the surface of the coated titanium oxide thin film to introduce a hydroxyl group;
3) a drug adhering step of adhering the drug onto the titanium oxide thin film surface-modified by binding the functional group of the drug to the hydroxyl group of the titanium oxide thin film to form the drug layer; and
4) an oligonucleotide adhering step of adhering oligonucleotide onto the drug layer by binding oligonucleotide to the drug to form the oligonucleotide layer. See FIG. 1.

$TiO_{2-x}N_x$ ($0 \leq x \leq 1$)  Chemical Formula 1

The titanium oxide in the present invention may be titanium dioxide ($TiO_2$), $TiO_{2-x}N_x$ ($0.001 \leq x \leq 1$), or the mixture thereof.

In the present invention, as the metal stent, a metal stent known in the art may be used without considering a shape, a length, a weight, or the like. Preferably, a skeleton of the metal stent may have an elastic shape so that the shape is not changed by pressure in vessel and other environmental affects while the metal stent stays in the vessel for a long period of time and the stent has excellent mobility, and a material thereof may be an anti-corrosive and harmless material. For example, a stent disclosed in Korean Patent Laid-Open Publication No. 10-2000-0069536, 10-1999-0035927, 10-1999-0087472, 10-2002-0093610, 10-2004-0055785, or the like, may be used.

In detail, the metal stent may be preferably made of a biocompatible metal material such as stainless steel, nitinol, tantalum, platinum, titanium, cobalt, chromium, a cobalt-chromium alloy, a cobalt-chromium-molybdenum alloy, and the like. In addition, other biocompatible metal material known in the art or a material bound to a biocompatible metal material may be used.

In the present invention, in the titanium oxide coating step (Step 1), the titanium oxide thin film may be coated onto the surface of the metal stent for 1 to 6 hours by transferring a titanium precursor, carrier gas, and reaction gas and generating plasma in a plasma vacuum chamber.

The titanium precursor may be at least one selected from a group consisting of titanium butoxide, tetra-ethyl-methyl-amino-titanium, titanium ethoxide, titanium isopropoxide, and tetra-methyl-hepta-diene-titanium, and any titanium precursor known in the art may be used as long as the precursor has excellent deposition characteristics at the time of depositing the titanium oxide onto the metal stent using the plasma enhanced chemical vapor deposition method.

In the present invention, as the carrier gas, at least one selected from a group consisting of nitrogen, argon, and helium may be used, and as the reaction gas, at least one selected from water vapor, ozone, and oxygen may be used. Here, nitrogen-doped titanium oxide may be formed by adding nitrogen to the reaction gas.

More specifically, in the present invention, the titanium oxide may be deposited on the surface of the metal stent using the titanium precursor by the plasma enhanced chemical vapor deposition method. In this case, a plasma enhanced chemical vapor deposition apparatus known in the art may be used. For example, a plasma enhanced chemical vapor deposition apparatus disclosed in Korean Patent Application Nos. 10-2005-0058926, 10-2001-0007030, 10-1990-0013643, or the like, may be used. Preferably, as shown in FIG. 2, a plasma enhanced chemical vapor deposition apparatus having a shape in which a titanium wire G capable of fixing a stent H in a plasma vacuum chamber is installed, a reduced pressure pump B is connected to the plasma vacuum chamber, a bubbler C filled with a precursor and gas tanks E and F are connected so that titanium precursor vapor may be injected into the plasma vacuum chamber together with gas, and the bubbler is connected to another gas tank D may be used.

Before the titanium oxide is deposited onto the metal stent, a process of fixing the metal stent into the plasma vacuum chamber and pre-treating the surface of the metal stent to wash the surface may be performed. The pre-treating process is performed in order to improve deposition strength between the stent and the titanium oxide thin film by maintaining a temperature in the plasma vacuum chamber at 200 to 600° C. and flowing argon and oxygen mixed gas.

In the present invention the titanium oxide of [Chemical Formula 1] deposited onto the metal stent may have two forms. One may be titanium dioxide ($TiO_2$) formed by binding between titanium and oxygen, and the other may be $TiO_{2-x}N_x$ ($0.001 \leq x \leq 1$) in which titanium dioxide ($TiO_2$) formed by binding between titanium and oxygen is doped with nitrogen.

A crystalline structure of the titanium oxide is not considered. For example, the crystalline structure may be a rutile form, an anatase form, a brookite form, or the like. The titanium oxide thin film is coated onto the surface of the metal stent by introducing the carrier gas in the chamber and the titanium precursor in order to deposit the titanium oxide thin film coating onto the metal stent using the plasma enhanced chemical vapor deposition method and generating plasma while flowing the reaction gas. In this case, the two forms of the titanium oxide may be determined according to a kind and flux ratio of the flowing reaction gas. Here, the carrier gas and the titanium precursor may be introduced into the plasma vacuum chamber by flowing at least one gas selected from the group consisting of nitrogen, argon, and helium as the carrier gas together with the titanium precursor. At the same time, in the case of generating the plasma while flowing only oxygen, titanium dioxide is deposited onto the surface of the metal stent, and in the case of generating plasma while flowing oxygen together with nitrogen, nitrogen-doped titanium oxide ($TiO_{2-x}N_x$ ($0.001 \leq x \leq 1$)) is deposited onto the surface of the metal stent.

Therefore, in order to deposit titanium dioxide ($TiO_2$) onto the metal stent, at the time of selecting the carrier gas, the carrier gas that does not include nitrogen may be preferable. It was proven that titanium oxide was biologically and biochemically stable as described above, and in the case of nitrogen-doped titanium oxide ($TiO_{2-x}N_x$ ($0.001 \leq x \leq 1$)), the fact that when titanium dioxide is doped with nitrogen, the anti-thrombotic effect was further improved was already reported by Kastarti A. and 12 others (Kastarti A., Mehilli J., Pache J., Kaiser C., Valgimigli M., Kelbaek H., Menichelli M., Sabate M., Suttorp M. J., Baumgart D., Seyfarth M., Pfisterer M. E., Schomig A., N. Engl. J. Med., 356, 1030, 2007).

According to the present invention, in order to introduce the titanium precursor into the plasma vacuum chamber, it may be preferable to generate gaseous titanium precursor using the bubbler and then introduce the gaseous titanium oxide. Here, the gaseous titanium precursor may be transferred into the plasma vacuum chamber by pre-heating the bubbler at a temperature suitable for generating the vapor phase in a range of room temperature to a boiling point of the titanium precursor and allowing the carrier gas to pass through the bubbler. At this time, titanium dioxide and nitrogen-doped titanium oxide ($TiO_{2-x}N_x$ ($0.001 \leq x \leq 1$)) may be formed by mixing oxygen or oxygen and nitrogen together with the carrier gas to transfer them. When the titanium precursor, the carrier gas, and the reaction gas are introduced into the plasma vacuum chamber, the plasma may be generated in the plasma vacuum chamber to thereby be chemically deposited onto the surface of the metal stent. In this case, the flux of the carrier gas may be 50 to 500 sccm, preferably 100 to 200 sccm, and the reaction gas may be injected at a flux of 10% of that of the carrier gas, preferably, 10 to 100 sccm. Further, in the case in which the reaction gas is not only oxygen but a mixed gas formed of different gases, that is, oxygen and nitrogen, oxygen and nitrogen may be injected at a flux ratio of 1 to 9:9 to 1.

According to the present invention, the titanium oxide may be deposited onto the surface of the metal stent by introducing the titanium precursor, the carrier gas, and the reaction gas and generating the plasma in the plasma vacuum chamber. A discharge power of the plasma may be 1 to 300 W and a reaction time may be 1 to 6 hours. Preferably, the plasma discharge may be performed at 5 to 200 W for 3 to 5 hours.

In the titanium oxide thin film coated-metal stent obtained after the above-mentioned process, a thickness of the titanium oxide thin film may be 10 to 500 nm, preferably 50 to 100 nm.

According to the present invention, in the surface modifying step (Step 2), the surface of the titanium oxide thin film may be modified for 10 minutes to 2 hours by transferring water vapor, or oxygen and hydrogen into the plasma vacuum chamber and generating non-thermal plasma.

According to the present invention, as the drug in step 3), at least one of abciximab, ALA and heparin may be selected and adhered.

More specifically, in the metal stent coated with the titanium oxide thin film by the plasma enhanced chemical vapor deposition method, in order to adhere the drug to the surface of the titanium oxide thin film, the surface of the titanium oxide thin film may be modified in a form in which the hydroxyl group (—OH) is introduced. The surface modification method may be performed in the plasma vacuum chamber used for forming the titanium oxide, and water vapor ($H_2O$) is transferred from an external introduction tube connected to the plasma vacuum chamber into the plasma vacuum chamber at a reduced pressure of $1 \times 10^{-3}$ to 1 torr, preferably $1 \times 10^{-2}$ to $1 \times 10^{-1}$ torr. Alternatively, mixed gas of hydrogen and oxygen may be used instead of water vapor. In this case, a flux of the water vapor or the mixed gas of hydrogen and oxygen may be 1 to 50 sccm based on a stent unit body. When the water vapor or the mixed gas of hydrogen and oxygen is introduced into the plasma vacuum chamber and the plasma is generated, oxygen in the surface of the titanium dioxide layer or the nitrogen-doped titanium oxide ($TiO_{2-x}N_x$ ($0.001 \leq x \leq 1$)) may be modified into the hydroxyl group.

At this time, the surface of the titanium dioxide layer or the nitrogen-doped titanium oxide ($TiO_{2-x}N_x$ ($0.001 \leq x \leq 1$)) layer may be modified into the surface in which the hydroxyl group is introduced by carrying out the reaction at a discharge power of the plasma of 1 to 300 W for 10 minutes to 2 hours, as a reaction condition.

The reason for modifying the titanium oxide thin film coated onto the metal stent into the surface in which the hydroxyl group is introduced is as follow. In views of chemical structural characteristics, since the drugs of the present invention have a functional group such as a carboxyl group, an aldehyde group, an alcohol group, or the like, it may be easy to bind the drug to the surface of the titanium oxide thin film through a dehydrogenation reaction by chemically reacting with the hydroxyl group in the surface of the modified titanium oxide thin film under an acidic condition.

In addition, in the drug and the titanium oxide thin film that are bound to each other by the principle as described above, after the drug is bonded thereto, various functional groups in the drug may be physically bonded to the surface of the stent to thereby be adhered to the surface of the stent in several layers. Therefore, at the time of inserting the drug eluting stent into blood vessel in body, the drug may be delayed-released while the physically bonded drug is separated from the drug eluting stent, and since the titanium oxide, and the drug may maintain their original structures, the drug may stably remain on the surface of the metal after the release of the drug is completed.

In the present invention, the drug means a drug capable of inhibiting neointimal hyperplasia or thrombus adhesion, and an example thereof may include at least one drug selected from a group consisting of anti-cancer drugs, anti-inflammatory drugs, smooth muscle cell growth inhibitors, anti-thrombotic agents, and the like.

In more detail, at least one drug selected from molsidomine, linsidomine, nitroglycerin, hydralazine, verapamil, diltiazem, nifedipine, nimodipine, captopril, enalapril, lisinopril, quinapril, losartan, candesartan, irbesartan, valsartan, dexamethasone, betamethasone, prednisone, corticosteroid, 17-beta-estradiol, cyclosporine, mycophenolic acid, tranilast, meloxicam, Cerebrex, indomethacin, diclofenac, ibuprofen, naproxen, serpin, hirudin, hirulog, argatroban, sirolimus, rapamycin, rapamycin derivatives, paclitaxel, 7-hexanoyl-taxol, cisplatin, vinblasitne, mitoxantrone, combretastatin A4, topotecan, methotrexate, flavopiridol, actinomycin, ReoPro (abciximab), alpha lipoic acid, heparin, warfarin, aspirin, abiprofen, prostaglandin, and the like, may be used. Preferably, at least one selected from heparin, Reopro (abciximab), alpha lipoic acid, sirolimus, rapamycin, actinomycin, molsidomine, linsidomine, paclitaxel, and the like, may be used.

That is, as the drug adhered to the titanium oxide thin film, alpha lipoic acid (ALA) having the anti-inflammatory effect or abciximab and Heparin having the anti-thrombotic effect are used, such that the anti-inflammatory effect and the anti-thrombotic effect may be obtained at the time of grafting the stent in body.

One of these drugs may be physically and chemically bonded to the surface of the titanium oxide thin film to release the drug in the body, or at least two different kinds of drugs may be independently bonded to the surface of the titanium oxide thin film to release at least two kinds of drug, thereby fabricating a multiple drug eluting stent.

If the drug is a mixture of at least two kinds of drugs, each of the drugs may be directly dispersed onto the surface-modified titanium oxide thin film to be bonded to the surface, or at least two kinds of drugs are physically and chemically bound to each other by electrostatic interaction between drugs to be bonded to the titanium oxide thin film, hydrogen bond, or the like, to thereby be released in the body See FIG. 3. For example, when lipoic acid and ReoPro are bound to the titanium oxide thin film together with each other, since lipoic acid has the anti-inflammatory effect but lacks the anti-thrombotic effect, the anti-thrombotic effect may be improved by ReoPro.

In the present invention, in the drug adhering step (step 3), the obtained metal stent including the titanium oxide thin film in which the hydroxyl group is introduced in the surface modification step (step 2) may be injected into an independent reactor known in the art and mixed with the drug, deionized water or an organic solvent may be further injected thereto, as needed, followed by stirring in an acidic solution under inert atmosphere, thereby performing the reaction.

In the present invention, the oligonucleotide in step 4) may include DNA, RNA, and a synthetic isoform thereof. In more detail, the oligonucleotide may be selected from a group consisting of genomic DNA (gDNA), complementary DNA (cDNA), plasmid DNA (pDNA), messenger RNA (mRNA), transfer RNA (tRNA), ribosomal RNA (rRNA), small interfering RNA (siRNA), micro RNA (miRNA), and antisense-oligonucleotide.

The oligonucleotide may exist in nature or be synthesized and derived from human, animals, plants, bacteria, virus, or the like. The oligonucleotide may be obtained by a method in the art.

In the present invention, in the oligonucleotide adhering step (step 4), a functional group of the oligonucleotide may be adhered to the functional group of the drug by at least one bond of a hydrogen bond, a dipole-dipole bond, an induced dipole bond, and a disulfide bond (S—S bond) therebetween.

The oligonucleotide layer adhered onto the drug layer has advantages in that the oligonucleotide may be efficiently delivered into cells by the bond and the proliferation of the vascular smooth muscle cells may be inhibited without adverse effects such as thrombus, inflammation, and the like.

The present invention provides a gene delivery stent using titanium oxide thin film coating, the gene delivery stent including: a titanium oxide thin film obtained by coating a surface of a metal stent with $TiO_2$, $TiO_{2-x}N_x$ ($0.001 \leq x \leq 1$), or a mixture thereof and modifying the coated surface to introduce a hydroxyl group; a drug layer containing a drug having a functional group bound to a hydroxyl group of the titanium oxide thin film to thereby be adhered onto the titanium oxide thin film; and an oligonucleotide layer containing oligonucleotide bound to the drug to thereby be adhered onto the drug layer.

In the gene delivery stent according to the present invention, the titanium oxide thin film may be the titanium dioxide ($TiO_2$) thin film or the nitrogen-doped titanium oxide ($TiO_{2-x}N_x$ ($0.001 \leq x \leq 1$)) thin film.

In the gene delivery stent according to the present invention, the drug may be at least one of abciximab, ALA, and heparin.

In the gene delivery stent according to the present invention, the oligonucleotide may be selected from a group consisting of gDNA, cDNA, pDNA, mRNA, tRNA, rRNA, siRNA, miRNA, and antisense-oligonucleotide.

Advantageous Effects

The gene delivery stent using titanium oxide thin film coating according to the present invention is fabricated by coating the surface of the implantable metal stent with the titanium oxide, modifying the surface of the coating layer, and adhering the drug and the gene to the modified surface, such that the titanium oxide thin film and the anti-inflammatory or anti-thrombotic drug may stably remain in a surface of the metal even though elution of the gene and the drug is completed, thereby reducing late thrombosis and metal allergy. In addition, the gene capable of inhibiting growth of cells may be transfected into the cell, thereby preventing vascular restenosis in the stent region.

The gene delivery stent using titanium oxide thin film coating according to the present invention fabricated by the above-mentioned method may be loaded with a drug having anti-inflammatory and anti-thrombotic effects and at the same time, deliver a gene capable of inhibiting proliferation of vascular smooth muscle cells. Accordingly, late thrombosis and metal allergy may be reduced, and vascular restenosis in the stent region may be prevented, thereby making it possible to increase treatment effects of the bare metal stent.

BEST MODE (1) Titanium oxide thin film coating on surface of metal

A metal plate having a size of 1 cm×1 cm was fabricated in a disk shape using stainless steel was fabricated among materials used for a stent, and titanium oxide thin film coating was performed on a surface of the metal plate.

Figure 1:
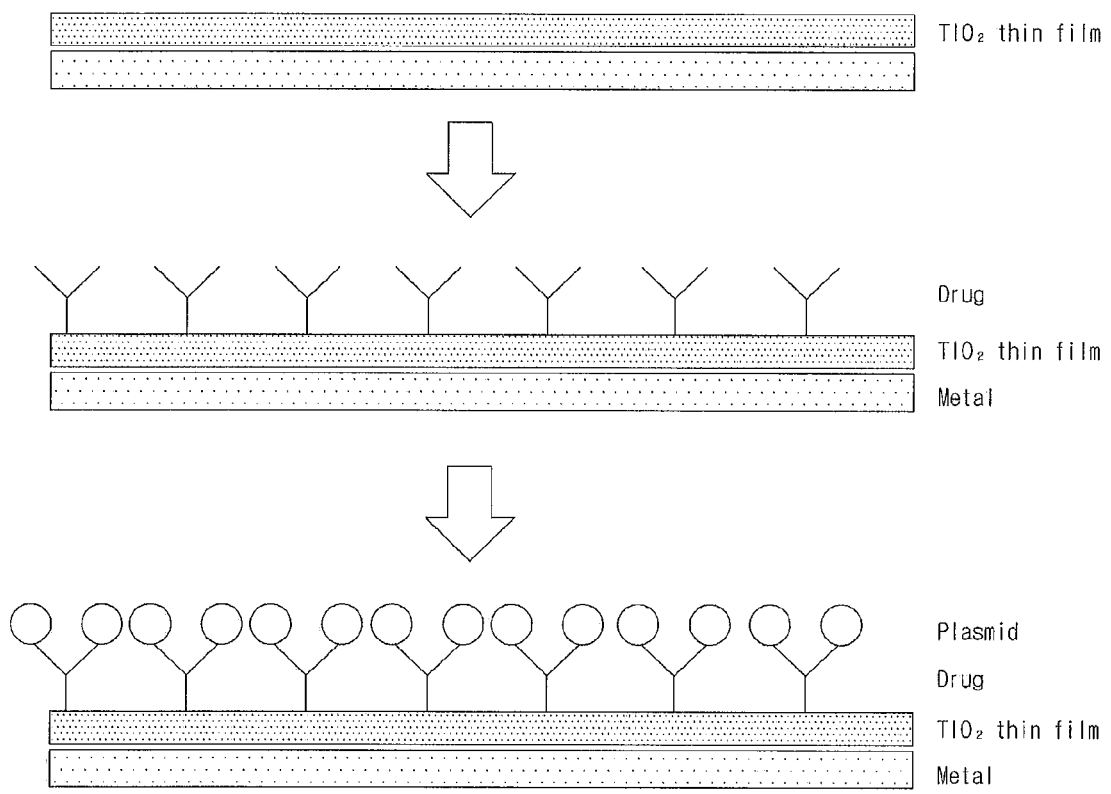
FIG. 1 is a view showing a process of sequentially coating a titanium oxide thin film and a drug on a surface of a metal stent and coating oligonucleotide thereon again in a gene delivery stent using titanium oxide thin film coating according to an exemplary embodiment of the present invention.
Figure 2:
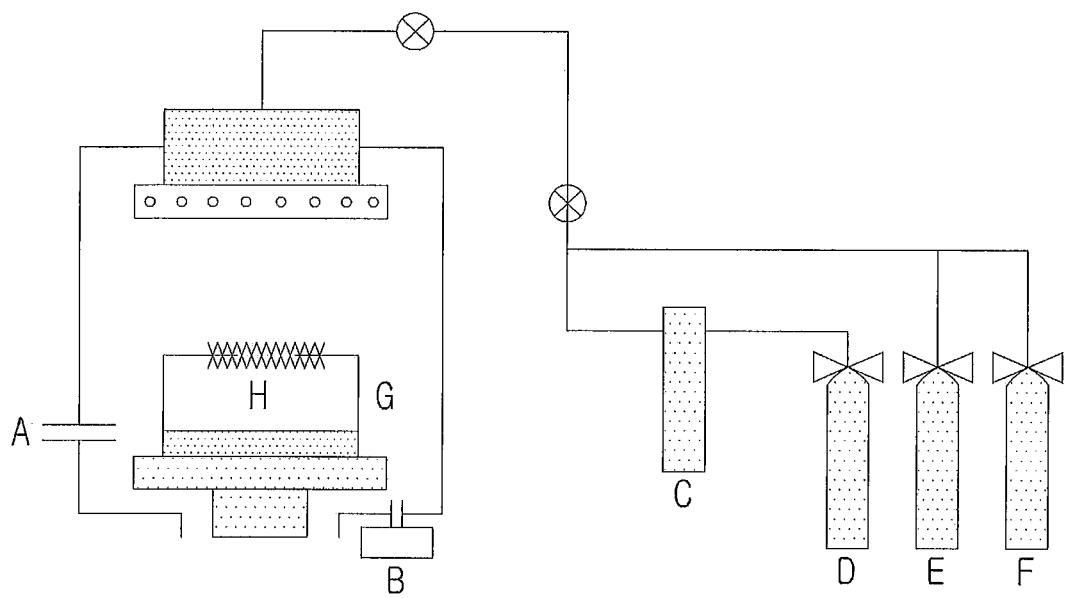
FIG. 2 is a mimetic view of a PECVD apparatus for coating titanium dioxide or nitrogen-doped titanium oxide ($TiO_{2-x}N_x$ (0.001≤x≤1)) used in the gene delivery stent using titanium oxide thin film coating according to the exemplary embodiment of the present invention.
Figure 3:
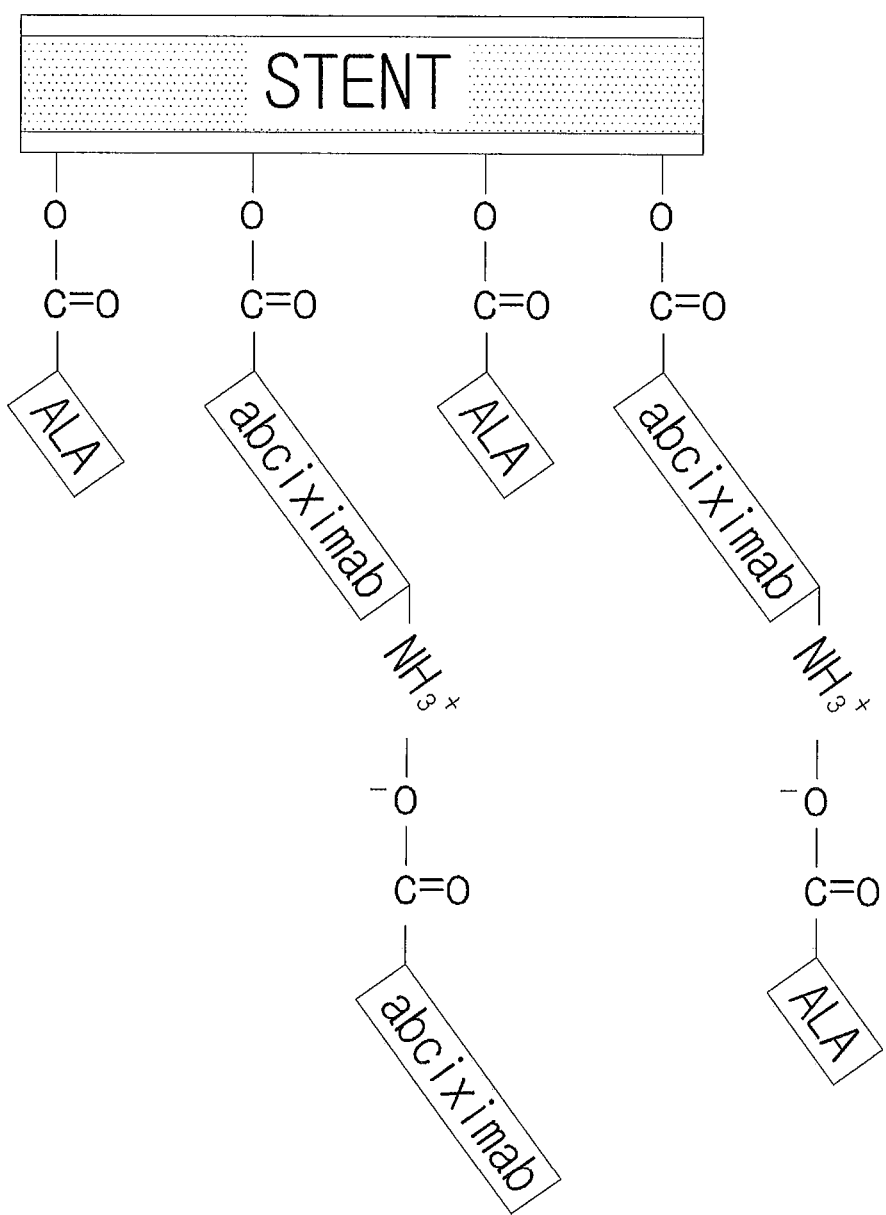
FIG. 3 is a mimetic view of a state in which alpha-lipoic acid (ALA) is adhered to the titanium oxide thin film in the gene delivery stent using titanium oxide thin film coating according to the exemplary embodiment of the present invention.

The metal plate was fixed to a plasma generator as a stent H shown in FIG. 2 in a vacuum chamber connected to a radio frequency (RF) plasma generator generating plasma and a vacuum pump, and a temperature of the plasma vacuum chamber was maintained at 400°. Firstly, in order to improve adhesion between a substrate of the metal plate and a thin film, the surface of the metal was subjected to a plasma pre-treatment process by flowing argon and oxygen before thin film coating to wash the surface of the metal. Titanium isopropoxide was put into a bubbler evaporator, mixed with oxygen, which was reaction gas using argon (Ar), which was carrier gas while maintaining a temperature of the bubbler at 50°, and then introduced in a reaction chamber, followed by generating plasma to perform a reaction for 4 hours, thereby coating the surface of the metal plate with a titanium dioxide thin film. In this case, a flow rate of argon (Ar), which was the carrier gas, was 100 sccm, and a flow rate of oxygen, which was the reaction gas, was maintained at 20 sccm. Discharge power was variously applied in a range of 5 to 200 W to coat the thin film. In order to fabricate a nitrogen-doped titanium dioxide thin film, the above-mentioned experimental conditions were equally maintained except that argon, oxygen, and nitrogen were supplied at flow rates of 100 sccm, 10 sccm, and 1 sccm, respectively.

The discharge power may be variously applied from 5 to 200 W at the time of coating the titanium dioxide thin film, but it was confirmed that as the larger the discharge power, the higher the surface roughness. Root mean square (Rms) values of results obtained by an atomic force microscope (AFM) of the thin film fabricated for 4 hours while changing discharge power at 5, 10, and 15 W were shown in the following Table 1.

TABLE 1

| Sample | NT5 | NT10 | NT25 | T5 | T10 | T15 |
|--------|-----|------|------|-----|------|--------|
| Rms | 3.571 | 5.142 | 7.119 | 7.760 | 9.403 | 13.862 |

T: titanium dioxide coated thin film, NT: nitrogen-doped titanium dioxide coated thin film, numbers (5, 10, 15): discharge power applied at the time of depositing titanium dioxide thin film As shown in Table 1, it was confirmed that in the case of the nitrogen-doped thin film, the surface was more uniform than in the case of the titanium dioxide thin film and the lower the discharge power, the more uniform the obtained thin film. It was known that the roughness of the thin film affects blood compatibility, and as the surface roughness is reduced, blood compatibility becomes excellent.

In addition, the thin film fabricated at 5 W had the lowest surface roughness. Therefore, all of the titanium dioxide thin film deposition for surface modification was performed while fixing discharge power at 5 W and maintaining a temperature 400° C. for 4 hours, thereby fabricating a stent coated with titanium dioxide.

Figure 4:
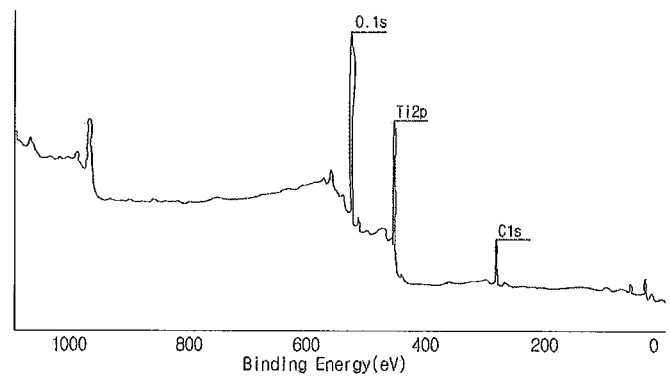
FIG. 4 is graphs obtained by electron spectroscopy for chemical analysis (ESCA) of a $TiO_2$ thin film deposited at 5 W and 400° C. for 4 hours in the gene delivery stent using titanium oxide thin film coating according to the exemplary embodiment of the present invention.
Figure 4:
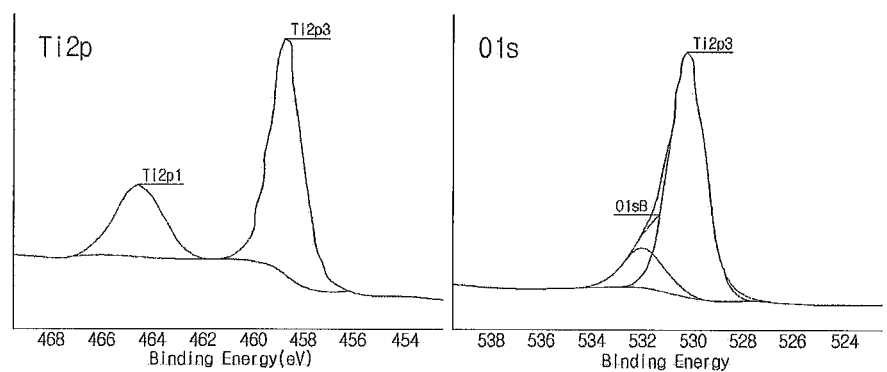

In FIG. 4 showing results of ESCA of the titanium dioxide thin film fabricated at 5 W, peaks corresponding to $Ti^{4+}$ in $TiO_2$ were confirmed at 458.8 eV (2p3/2) and 464.7 eV (2p1/2), and an O1s peak corresponding to a Ti—O bond in $TiO_2$ was confirmed at 530.4 eV.

Figure 5:
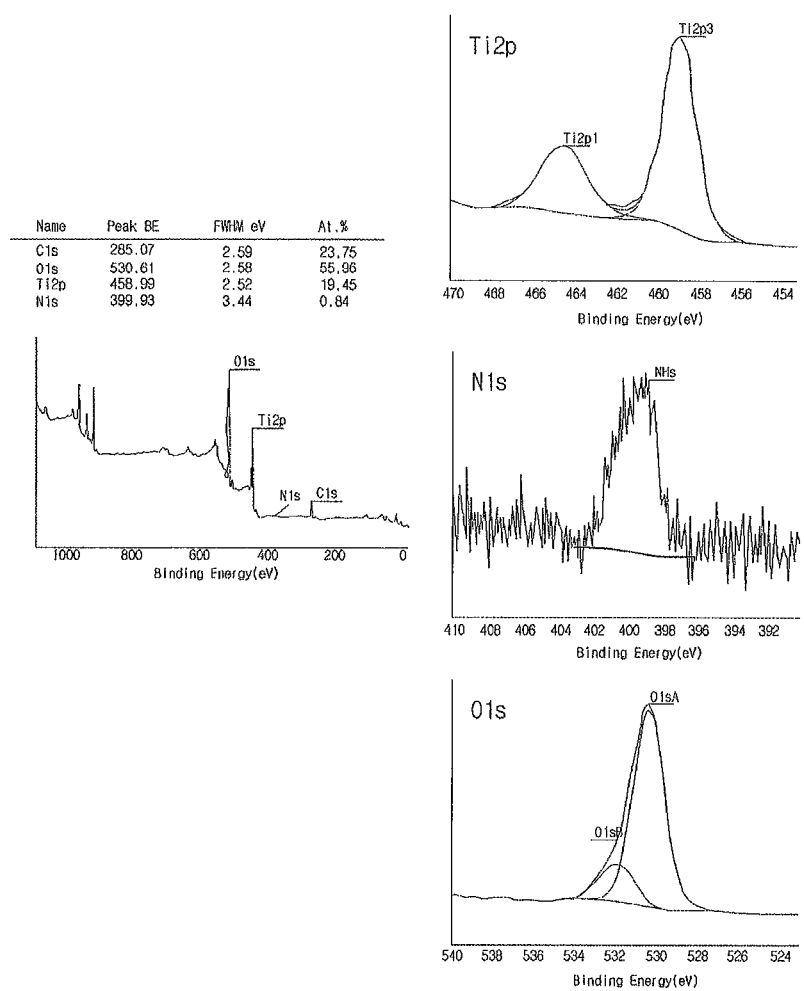
FIG. 5 is graphs obtained by ESCA of a nitrogen-doped $TiO_2$ thin film deposited at 5 W and 400° C. for 4 hours in the gene delivery stent using titanium oxide thin film coating according to the exemplary embodiment of the present invention.

In FIG. 5 showing results of ESCA of the nitrogen-doped titanium dioxide thin film, Ti peaks and O1s peaks were confirmed at positions similar to that in the titanium dioxide thin film, and an N1s peak was confirmed at 399 eV at a content ratio of 0.8%, such that it was confirmed that the surface of the titanium dioxide was doped with nitrogen.

(2) Modification of titanium oxide thin film coating layer for generating hydroxyl group In order to adhere the drug onto the surface of the coated titanium dioxide, a functional group capable of chemically binding to a functional group in drug molecules needs to exist in the surface of the titanium oxide.

Therefore, in the present invention, in order to introduce —OH group in the surface of the titanium dioxide layer capable of chemically binding to the drug, the surface of the thin film was modified by non-thermal plasma using deionized water ($H_2O$). After the metal plate coated with titanium dioxide was fixed to a tubular non-thermal plasma reactor made of Pyrex and the bubbler was filled with tertiary deionized water, water vapor was introduced into the plasma reactor at 10 sccm and discharge power was changed in a range of 10 to 100 W, thereby modifying the titanium dioxide thin film for 10 minutes using a non-thermal plasma process.

In order to introduce the hydroxyl group in the surface of the titanium dioxide thin film, after the surface was modified using $H_2O$, the surface was washed with deionized water once, and then a contact angle was measured. Results between the discharge power and the contact angle applied for modification were shown in FIG. 6.

Figure 6:
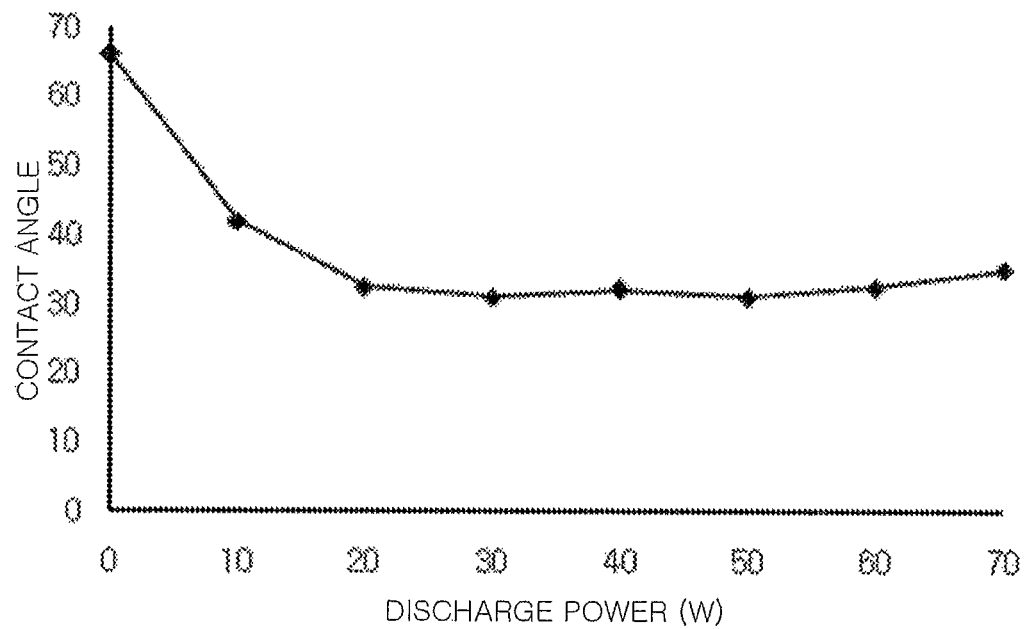
FIG. 6 is a graph showing a contact angle change according to a discharge power applied to surface modification in the gene delivery stent using titanium oxide thin film coating according to the exemplary embodiment of the present invention.

As a result, as shown in FIG. 6, entirely, the contact angle was reduced by about 40 (degrees) than the contact angle before modification, it was confirmed that a hydrophilic functional group was introduced in the surface. In addition, it was confirmed that the contact angle was reduced when the applied discharge power was in a range of 20 to 50 W, and as the discharge power became higher than 60 W, there was an increasing tendency in contact angle.

This may be because as the discharge power was increased, the titanium dioxide thin film, which was a target for modification, was slightly etched by the plasma, or a structure of titanium dioxide was changed.

(3) Drug adhesion

The used drugs were as follows.
(1) α-lipoic acid (Thiocticaid (ALA); Bukwang Pharm. Co. Ltd)
(2) Abciximab (ReoPro; Eli Lilly and Company, Indianapolis, Ind.)
(3) Heparin sodium salt (Grade1-A, From Porcine Intestinal Mucosa, Sigma-Aldrich)
(4) 1-(3-Dimethylaminopropyl)-3-ethylcarbodiimide methiodide (DCC; 98%, Alfa Aesar)
(5) 4-(Dimethylamino)pyridine (DMAP; 99%, Sigma-Aldrich Co.)
(6) Sodium bicarbonate (99%, Dae Jung Chemicals & Metals Co., Ltd)

In order to adhere ALA onto the surface of the titanium dioxide coating layer, 0.0124 g of ALA, 0.005 g of sodium bicarbonate were sufficiently dissolved by adding 2 mL of deionized water, respectively, to prepare an ALA solution, 0.8915 g of DCC and 0.07 g of DMAP were dissolved in 150 mL of deionized water, respectively. 2 mL of the prepared ALA solution and 1.5 mL of the DMAP+DCC mixed solution were harvested, respectively, and put into a vessel, followed by mixing. Then, the mixed solution was left at 35° C. for 1 hour to activate the mixed solution, and the surface-modified metal plate fabricated in Surface-modified metal plate was put into the activated mixed solution and stored at 35° C. for 2 hours, thereby adhering the drug to the surface of the titanium dioxide layer.

Heparin was adhered by the same method except that 1.5 mL of the prepared DMAP+DCC mixed solution was put into 0.0065 g of heparin sodium salt.

Abciximab was adhered by the same method except that 1.5 mL of the DMAP+DCC mixed solution was put into 0.25 mL of abciximab.

(4) Gene adhesion

The drug adhered to the surface of the metal plated coated with titanium dioxide had various kinds of chemical functional groups. For example, there were a carboxyl group, an amine group, a disulfide (S—S) bond, and the like. A plasmid was put into an aqueous solution maintained at a pH of 6 to 7, and the stent containing the drug adhered thereto was added thereto and maintained at room temperature for a predetermined time (1 to 5 hours). In this case, various physical interactions were generated between various functional groups in the drug adhered to the surface of the metal plate coated with the titanium dioxide thin film and functional groups existing in the plasmid, such that the plasmid was adhered to the surface of the metal plate in several layers.

In order to confirm whether or not the gene was delivered from the metal plate composed of the titanium dioxide/drug/gene complex fabricated by the above-mentioned method, gWIZ-β-gal plasmid was purchased from Genlantis Company. When gWIZ-beta gal plasmid is delivered into the cells, the cells generate β-Galactosidase, wherein β-Galactosidase, which is an enzyme hydrolyzing β-galactoside, is used as a reporter gene in eukaryotic transfection experiment. In cells in which the gene is transfected, β-Galactosidase cleaves 5-bromo-4-chloro-3-indoyl-beta-D-galactopyranoside (X-gal) to generate blue precipitates. Since this blue color may be observed in tissue or cell through a microscope or by the naked eyes, it is possible to determine whether the gene was transfected or not.

Figure 7:
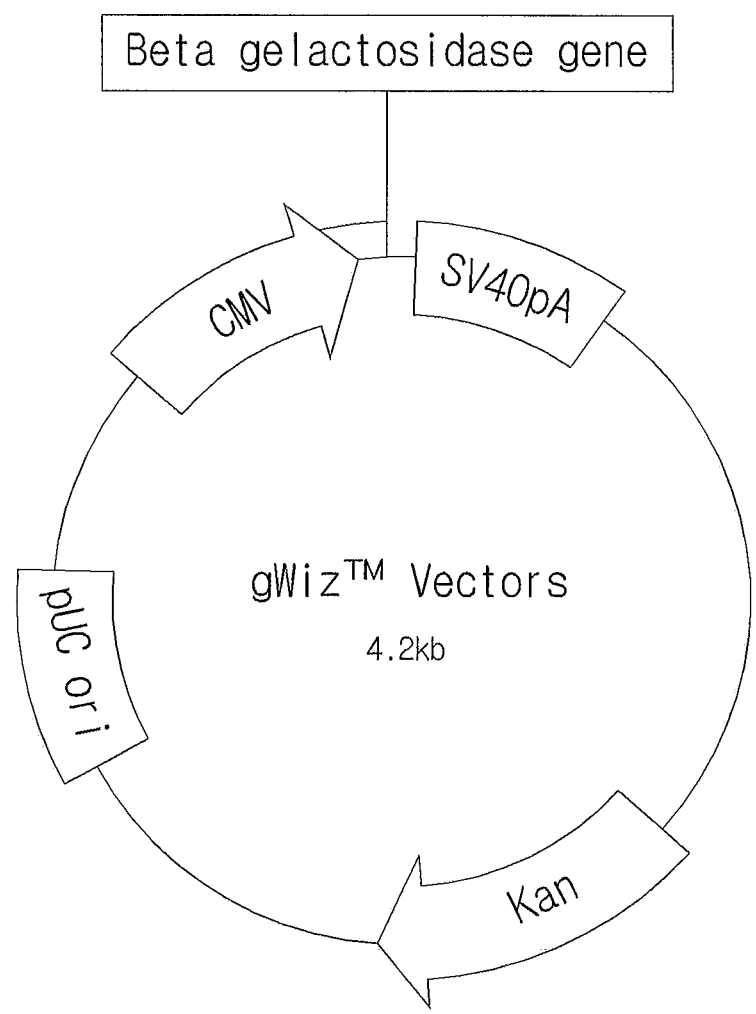
FIG. 7 is a simple mimetic view of a plasmid allowing whether or not the gene is transfected to be known by generating beta-galactosidase as a plasmid coated in the gene delivery stent using titanium oxide thin film coating according to the exemplary embodiment of the present invention.

FIG. 7 shows a simple mimetic view of the plasmid allowing whether or not the gene is transfected to be known by generating beta-galactosidase as gWIZ-β-gal plasmid.

Experimental Example 1

Quantification of Adhered Gene

The metal plate fabricated by the methods in Examples (1) to (3) was positioned on a 12-well plate, and a solution containing genes (total plasmid content: 20 ug/200 ul DW) was put onto the metal plate. After the metal plate was left for 8 to 12 hours, the metal plate was immersed again in sterile deionized water (DW) for 30 minutes to remove extra DNA non-specifically adhered thereto. A concentration of the plasmid in washing DW was measured using Nanodrop ND-1000 spectrophotometer (Thermo scientific, USA). After the plate was washed and dried in a sterile bench, subsequent experiments were performed. The amount of DNA adhered to the flask was estimated by arithmetically subtracting a measured amount of the DNA in the washing DW from initial 20 ug of plasmid according to the following Equation 1.

DNA binding amounts (ug)=20 ug−DNA amount (ug) in washing DW          Equation 1

Figure 8:
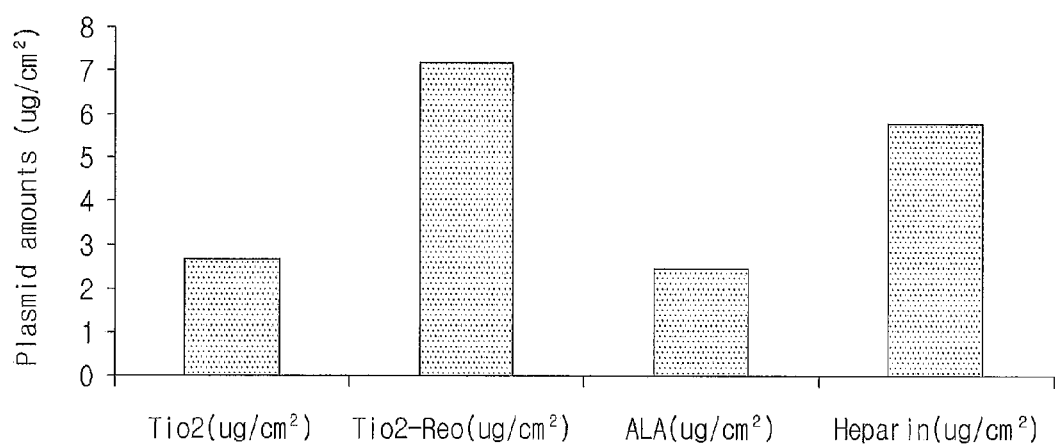
FIG. 8 is a graph showing an amount of genes coated on each of three drug (abciximab, heparin, ALA) coating layers in the gene delivery stent using titanium oxide thin film coating according to the exemplary embodiment of the present invention.

FIG. 8 is a graph showing the amount of the gene coated on each of three drug (abciximab, heparin, ALA) coating layers in the gene delivery stent using titanium oxide thin film coating according to the exemplary embodiment of the present invention. In FIG. 8, it may be confirmed that in the case of a $TiO_2$ single coating group, in the case of an abciximab coating group, in the case of a heparin coating group, and in the case of ALA coating group, amounts of plasmid coated at an area of 1 $cm^3$ were approximately 2.7 ug, 7.2 ug, 5.6 ug, and 2.5 ug, respectively.

Experimental Example 2

Intracellular Expression of Gene Eluted from Metal/Titanium Dioxide/Drug/Gene Complex In order to confirm whether or not functional deformation was generated in the plasmid after the gene was bound to the surface of the metal plate in a form of titanium/drug/gene (plasmid) complex (hereinafter, referred to as a metal flask), after the metal flask was generated, the gene was artificially separated, followed by measuring whether or not the gene had an activity.

In order to elute the gene from the metal flask, the metal flask was put in a 12-well plate, and 100 uL of 0.1×TE buffer (pH 8.0) was added thereto again and left at room temperature for 30 minutes. After 30 minutes, 0.1×TE buffer was harvested, and an amount of the eluted plasmid was measured using Nanodrop ND-1000 spectrophotometer (Thermo Scientific, USA).

In order to confirm whether or not the eluted plasmid was normally active, the gene was transfected in cells under in vivo conditions, using Lipofectamine 2000, which is a transfection product fabricated by Invitrogen Company. As described below, human embryonic kidney 293 T cells (HEK 293 T cell) were seeded in a 12-well plate at $1\times10^5$/well and cultured. After 24 hours, a culture medium was treated with 6 ug of the eluted plasmid using Lipofectamine, and after 4 hours, the culture medium was stirred, followed by continuously culturing for 48 hours. Then, X-gal staining was performed.

After fixing the cell, the cell was stained with an X-gal stain solution at 37° C. for 24 hours. Thereafter, in the case of observing whether the cell was stained or not, the positively stained cell was observed as a blue stained cell in an optical microscope.

Figure 9:
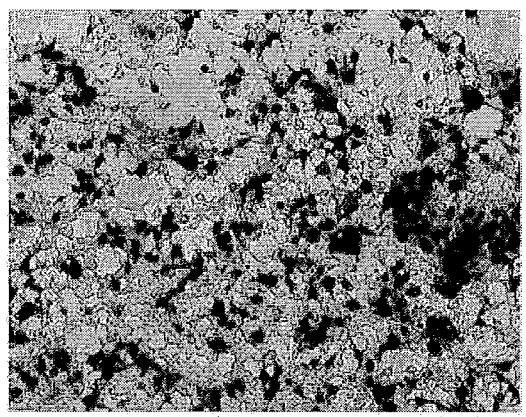
FIG. 9 is photographs showing that the genes are safely coated on a titanium oxide/Abciximab/plasmid composite layer, a titanium oxide/Heparin/plasmid composite layer, and a titanium oxide/ALA/plasmid composite layer without damage in functions of the gene, respectively, and all of the genes (g-Wiz lacZ plasmid) are normally expressed in cells, in the gene delivery stent using titanium oxide thin film coating according to the exemplary embodiment of the present invention.
Figure 9:
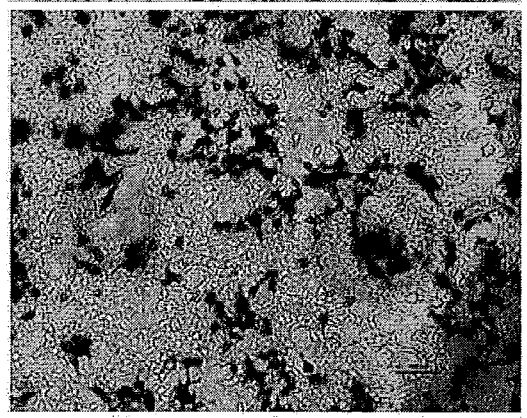
Figure 9:
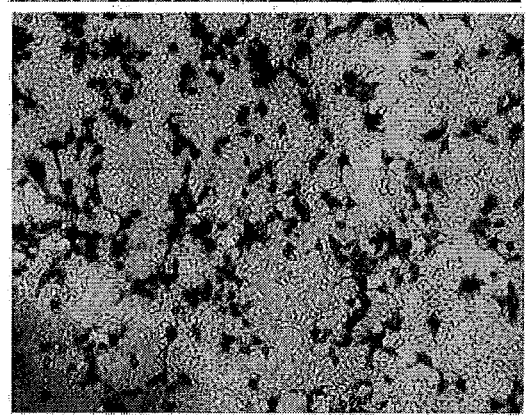

As a result, as shown in FIG. 9, it may be confirmed that the genes were safely coated on each of the gene delivery stents using titanium oxide thin film coating according to the exemplary embodiment of the present invention, that is, the titanium dioxide/abciximab/plasmid composite layer, the titanium dioxide/heparin/plasmid composite layer, and the titanium dioxide/ALA/plasmid composite layer without damaging the functions of the gene, and all of the genes (g-Wiz lacZ plasmid) were normally expressed in cells.

In addition, as shown in FIG. 9, it was confirmed that all of the plasmid eluted from abciximab, ALA, and heparin normally allowed the cell to generate β-galactosidase. As the result, it may be confirmed that the functions of the gene coated in the present invention were maintained.

Experimental Example 3

Confirmation of Whether or Not Genes are Delivered in Abdominal Wall of Rats for Experiment The metal flask fabricated in the Examples was grafted in abdominal wall of rats for the experimental. After 7 days of grafting, muscles of the abdominal wall were harvested and the X-gal staining was performed by the same method as that in Experimental Example 2. After staining, the muscle in abdominal wall was cut, and a stained site was confirmed.

Figure 10:
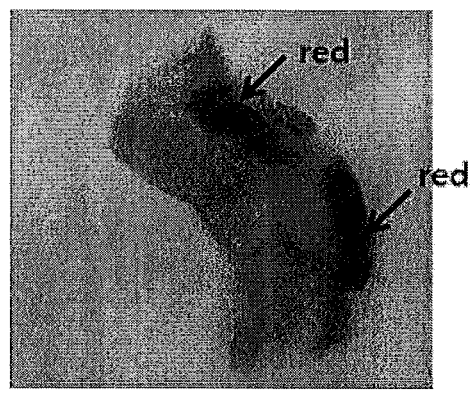
FIG. 10 is photographs showing that the genes are transfected into tissues after metal pieces coated with each of the titanium oxide/Abciximab/plasmid composite layer, the titanium oxide/Heparin/plasmid composite layer, and the titanium oxide/ALA/plasmid composite layer are grafted in bodies of rats for an experiment, in the gene delivery stent using titanium oxide thin film coating according to the exemplary embodiment of the present invention.
Figure 10:
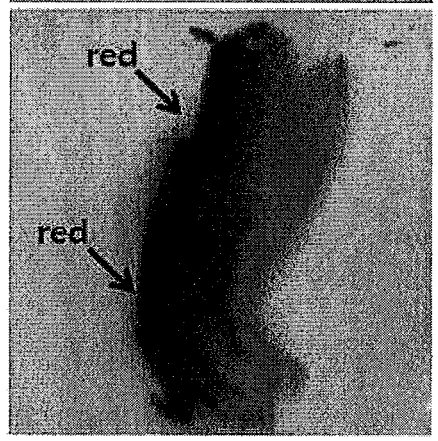
Figure 10:
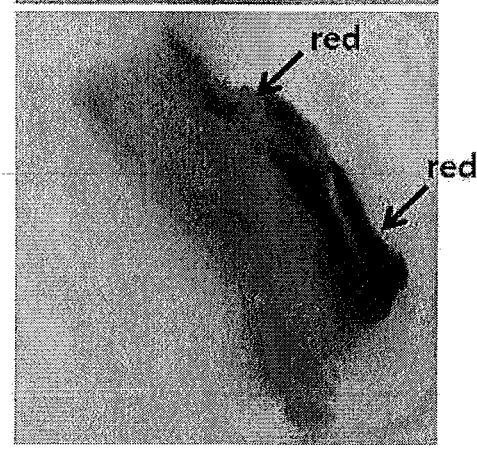

FIG. 10 is a photograph showing that the genes were transfected into tissues after the gene delivery stent using titanium oxide thin film coating according to the exemplary embodiment of the present invention, that is, metal pieces coated with each of the titanium dioxide/abciximab/plasmid composite layer, the titanium dioxide/Heparin/plasmid composite layer, and the titanium dioxide/ALA/plasmid composite layer were grafted in bodies of the rats for the experiment.

As shown in FIG. 10, it may be confirmed that the sites at which the tissue in the abdominal wall was stained as a blue color were observed by the naked eyes. The results shows that the β-gal gene-coated plate successfully transfected the gene in the abdominal tissue.

Figure 11:
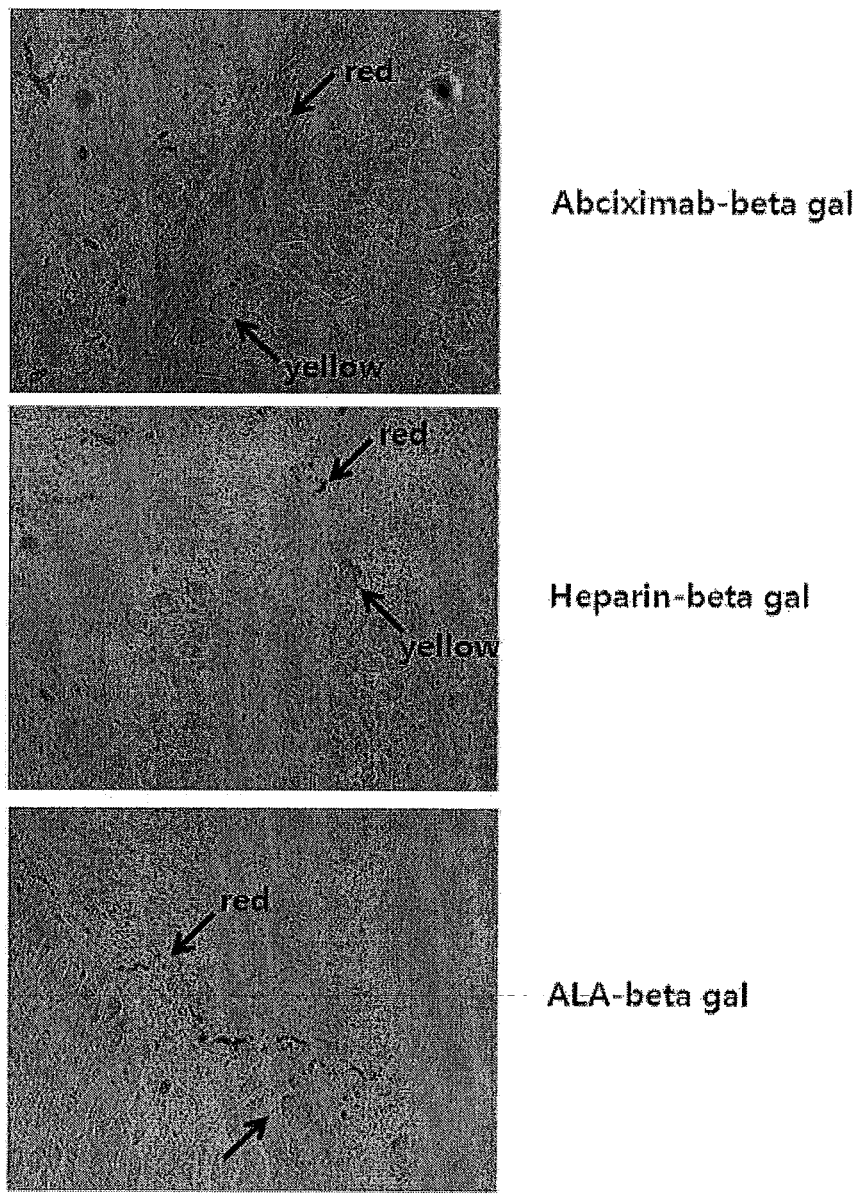
FIG. 11 is cross-sectional views of the tissues into which the genes are transfected after the metal piece coated with each of the titanium oxide/Abciximab/plasmid composite layer, the titanium oxide/Heparin/plasmid composite layer, and the titanium oxide/ALA/plasmid composite layer are grafted in bodies of rats for the experiment, in the gene delivery stent using titanium oxide thin film coating according to the exemplary embodiment of the present invention.

In addition, as shown in FIG. 11, it may confirmed that the cells of the tissue in which the gene was transfected by grafting the metal piece coated with each of the titanium dioxide/abciximab/plasmid composite layer, the titanium dioxide/Heparin/plasmid composite layer, and the titanium dioxide/ALA/plasmid composite layer, in the body of the rats for the experiment delivered the gene to a connective tissue (red arrow) on the abdominal wall, and at the same time, the stained sites were also observed in the tissue cells (yellow arrow) under the connective tissue by the microscope.

Experimental Example 4

Confirmation of Whether or Not Genes are Delivered in Vascular Smooth Muscle Cells In order to confirm whether or not the gene may be transfected in the vascular smooth muscle cell capable of being a main graft site of the stent besides the connective tissue and the muscle tissue from the plate coated with the gene as confirmed in Experimental Example 3, the vascular smooth muscle cells were directly cultured in the surface of the metal plate, followed by confirming whether the gene was transfected in the cell.

The vascular smooth muscle cells were separated from the porcine coronary artery separated in a sterile state. After separating the coronary artery from a heart of the pig, all of the connective tissues in the outside of the blood vessel were removed, and vascular endothelial cells were removed by scratching the inside of the blood vessel using forceps. The blood vessel tissue from which the connective tissue and the endothelial cell were removed was put into a solution containing collagenase, elastase, and tryptase and finely cut using scissors, followed by reacting with each other in a shaking culture equipment at 37 and 60 rpm for 60 minutes to separate the cells. Then, the separated cells were cultured in Dulbecco's Modified Eagles (DME) media. After culturing, the cultured cells were proliferated up to passage 3 to 4, and then the immuno-staining was performed using anti-smooth muscle actin Ab (anti-SMC Ab) to confirm that the proliferated cells were vascular smooth muscle cells. The confirmed cells were used in the subsequent experiments. The metal plate coated with β-gal gene was positioned in a 12-well plate, and the vascular smooth muscle cells were cultured thereon at $5 \times 10^4$/well using DME media containing 10% fetal bovine serum (FBS). After 7 days of culture, the metal plate in which the cells were cultured to thereby be adhered thereto was picked out and fixed, and then the staining was performed by the same method as the X-gal staining method in Experimental Example 2.

Figure 12:
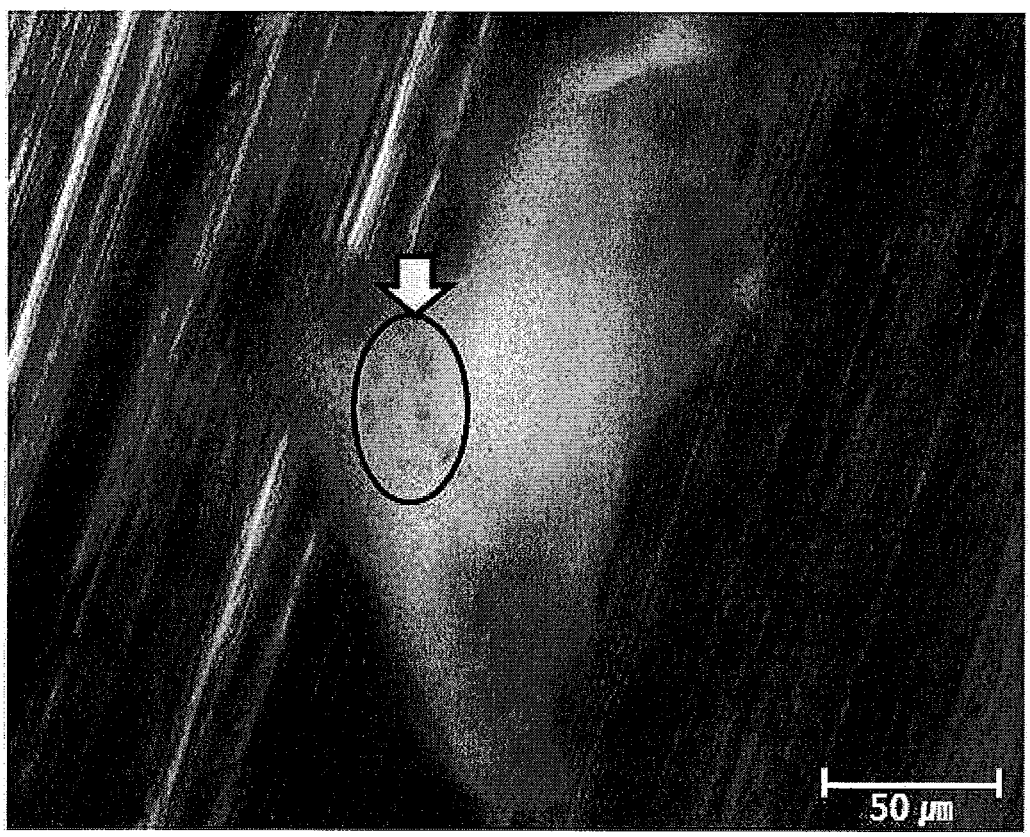
FIG. 12 is a photograph showing that when porcine coronary vascular smooth muscle cells are cultured on the metal pieces coated with the titanium oxide/Abciximab/plasmid composite layer, the genes are transfected into the cells.

The stained metal pieces were observed under a microscope. As a result, as shown in FIG. 12 (photograph showing that when porcine coronary vascular smooth muscle cells were cultured on the metal pieces coated with the titanium dioxide/abciximab/plasmid composite layer, the genes were transfected into the cells), it may be confirmed that the cells (arrow) adhered to the surface of the metal was observed as a blue stained cell. The result indicates that the metal/titanium dioxide/drug/gene complex may transfect the gene in the vascular smooth muscle cells.

The invention claimed is:

1. A method for fabricating a gene delivery stent using titanium oxide thin film coating, the method comprising:
   a) a titanium oxide coating step of coating a surface of a metal stent with a titanium oxide thin film consisting of titanium oxide ($TiO_2$), $TiO_{2-x}N_x$ wherein $0.001 < x < 1$, or a mixture thereof;
   b) a surface modifying step of modifying the surface of the coated titanium oxide thin film to introduce a hydroxyl group;
   c) a drug adhering step of adhering drugs onto the titanium oxide thin film surface-modified by binding a functional group of the drug to the hydroxyl group of the titanium oxide thin film to form a drug layer; and
   d) an oligonucleotide adhering step of adhering oligonucleotide onto the drug layer by binding oligonucleotide to the drug to form an oligonucleotide layer
   wherein in step b), the surface of the titanium oxide thin film is modified for 10 minutes to 2 hours by transferring water vapor, or oxygen and hydrogen into a plasma vacuum chamber and generating non-thermal plasma, and wherein applied discharge power is in the range of 20-50 W,
   wherein in step b), when water vapor is used, the water vapor is transferred from an external introduction tube connected to the plasma vacuum chamber into the plasma vacuum chamber at a reduced pressure of $1 \times 10^{-3}$ to 1 torr,
   wherein in step a) the titanium oxide thin film is coated onto the surface of the metal stent for 1 to 6 hours by transferring a titanium precursor, carrier gas, and reaction gas and generating plasma in a plasma vacuum chamber,
   wherein the carrier as is at least one selected from the group consisting of nitro en argon, and helium,
   wherein the reaction gas is at least one selected from the group consisting of water vapor, ozone, and oxygen, and
   wherein as the drug in step c), at least one of abciximab, alpha lipoic acid, and heparin is selected to thereby be adhered.

2. The method of claim 1, wherein the metal stent is made of stainless steel, nitinol, tantalum, platinum, titanium, cobalt, chromium, a cobalt-chromium alloy, or a cobalt-chromium-molybdenum alloy.

3. The method of claim 1, wherein the titanium precursor is at least one selected from a group consisting of titanium butoxide, tetra-ethyl-methyl-amino-titanium, titanium ethoxide, titanium isopropoxide, and tetra-methyl-hepta-diene-titanium.

4. The method of claim 1, wherein the oligonucleotide in step d) is selected from a group consisting of gDNA, cDNA, pDNA, mRNA, tRNA, rRNA, siRNA, miRNA, and anti-sense-oligonucleotide.

5. The method of claim 1, wherein in the oligonucleotide adhering step (step d), a functional group of the oligonucleotide is adhered to the functional group of the drug by at least one bond of a hydrogen bond, a dipole-dipole bond, an induced dipole bond, and a disulfide bond (S—S bond) therebetween.

* * * * *

UNITED STATES PATENT AND TRADEMARK OFFICE
CERTIFICATE OF CORRECTION

PATENT NO. : 9,533,074 B2  Page 1 of 1
APPLICATION NO. : 13/993896
DATED : January 3, 2017
INVENTOR(S) : Jin Sook Kwon et al.

It is certified that error appears in the above-identified patent and that said Letters Patent is hereby corrected as shown below:

In the Claims

Column 16, Line 15, Claim 1, delete "as" and insert -- gas --

Column 16, Line 16, Claim 1, delete "nitro en" and insert -- nitrogen, --

Signed and Sealed this
Fourth Day of April, 2017

Michelle K. Lee
*Director of the United States Patent and Trademark Office*